United States Patent [19]

Hanson

[11] Patent Number: 5,342,097
[45] Date of Patent: Aug. 30, 1994

[54] QUICK DISCONNECT MULTI-LINE CONNECTOR IN A DENTAL SYSTEM

[75] Inventor: Richard W. Hanson, Sherwood, Oreg.

[73] Assignee: MDT Corporation, Torrance, Calif.

[21] Appl. No.: 6,056

[22] Filed: Jan. 19, 1993

[51] Int. Cl.⁵ .................. F16L 34/00; A61C 19/00
[52] U.S. Cl. ........................ 285/25; 285/137.1; 285/131; 433/77; 433/126
[58] Field of Search ............... 285/25, 26, 137.1, 131; 433/77, 126

[56] References Cited

U.S. PATENT DOCUMENTS

| | | |
|---|---|---|
| 3,469,863 | 9/1969 | Riester et al. ............ 285/137.1 |
| 3,530,513 | 9/1970 | Maurer et al. ............... 433/77 |
| 3,640,552 | 2/1972 | Demler, Sr. et al. ........ 285/137.1 |
| 3,771,226 | 11/1973 | Lieb et al. .................. 433/77 |
| 3,960,393 | 1/1976 | Hosokawa et al. ......... 285/137.1 |
| 4,076,279 | 2/1978 | Klotz et al. ................ 285/137.1 |
| 4,445,859 | 5/1984 | Hoffmeister et al. ........ 433/77 |
| 4,464,113 | 8/1984 | Parmley ..................... 433/77 |
| 4,648,839 | 3/1987 | Timerdahl et al. .......... 433/77 |
| 4,887,850 | 12/1989 | Albrecht .................. 285/137.1 |
| 4,938,509 | 7/1990 | LaPlante .................... 285/26 |

FOREIGN PATENT DOCUMENTS 1522473  4/1968  France ................... 285/131

Primary Examiner—Eric K. Nicholson
Attorney, Agent, or Firm—Trask, Britt & Rossa

[57] ABSTRACT

A quick disconnect multi-line utility connector including a first body member configured and sized to permit passage, end to end, through the hollow interior of an upstanding tubular mounting post. The first body member is connected to a second body member associated with primary utility support conduits at a junction box.

10 Claims, 3 Drawing Sheets

QUICK DISCONNECT MULTI-LINE CONNECTOR IN A DENTAL SYSTEM

BACKGROUND OF THE INVENTION

1. Field of the Invention

This invention relates to post mounted dental delivery systems. It is particularly directed to multi-line delivery systems used to connect control head units to the necessary fluid utilities.

2. State of the Art

Post mounted dental delivery systems commonly require utility connections to water, air, vacuum, and drain service lines. Such systems typically include a hollow mounting post and a delivery arm separating the utility sources from a handpiece control head. The utility sources are normally accessible at a junction box at the base of the post. Primary utility supply lines are conventionally tapped or otherwise connected to secondary supply lines at the junction box. The secondary supply lines are fed from the junction box, through the post and arm, to the control head. The arm may be connected to the post and/or the control head through articulated connecting structures. Dental handpieces (control head units) are operably associated with the secondary utility supply lines through the control head.

Individual utility lines are conventionally fed through the arm, post and any articulating joints to connect the control head units to the appropriate utility sources. Trained field personnel have been required for installation to assure that leak proof couplings are effected with the various utilities. In addition, local building codes subject field connections to obligatory inspections. A significant amount of coordination is required to accomplish the delivery, installation and inspection of post mounted dental delivery systems of current construction.

Field assembly problems and costly customer down time are the primary drawbacks experienced with currently available post mounted dental delivery systems. Control heads, unit hand devices, accessories, delivery arms, support arms, and mounting posts are now packed and shipped unassembled. It is not practical to ship these components in assembled condition because of the need for feeding utility lines through the post and arm at the installation site. Packing errors occur, and errors in field assembly of the various components are not uncommon. Field assembly errors in utility connections may lead to water running into valves and turbines meant for air. Coordination with trained field service representatives and inspectors is required during assembly and installation. Such coordination requirements often lead to lengthy delays.

Modification or replacement of post mounted dental delivery systems has required the complete disassembly and reassembly of the control head, hand devices, joint components (such as hub washers), support arms, and mounting post components of the system by trained service representatives. Utility service has been interrupted while new connections have been created. Extended equipment down time due to inconvenient service schedules and packaging and shipping errors has proven frustrating during refurbishment, as well as during new installation.

There is a need for a system which permits the installation of new equipment, replacement of outdated or worn out equipment, addition of new service capabilities, and modification of dental delivery system configurations quickly and easily. There thus remains a need for a system by which utility connections can easily and safely be made by the user or by installation personnel that have not been specially trained. It would also be desirable for such a system to allow preassembly and verification of the various system components prior to shipping.

SUMMARY OF THE INVENTION

The present invention provides a quick disconnect multi-line utility connector of small cross section. The connector includes first and second body members. The first body member is structured and arranged so that it can be connected to the secondary utility supply lines associated with the control head. These supply lines may be provided in an umbilical arrangement. The first body member is configured and sized to permit its passage, end to end, through the hollow interior of an upstanding tubular mounting post. Typically, the first body member is passed from an arm or control center at the top of the post to the connection location of the primary utility supply lines at or near the base of the post. The second body member is structured and arranged to connect to the primary utility supply lines and to couple with the first body member, thereby bringing the primary and secondary utility supply lines into fluid communication through the connector. The second body member may be installed at the delivery site prior to delivery of the other components of the system, thereby eliminating the need for close coordination.

The connector of this invention constitutes a means of connection whereby untrained personnel may install preassembled new or repaired control head units safely, easily and in a leak-free manner. It also permits factory preassembly of a control head and its accessories, the necessary secondary utility lines (preconnected to a first body member of the connector), and a support arm.

The connector is sized to accommodate insertion and feeding of the first body member and its attached utility line umbilical through the inner diameter of an existing mounting post and its fittings; without first requiring disassembly of the mounting post, connector, umbilical, control head, support arms, or hand units.

Each body member includes a plurality of utility line fittings projecting from a base. The bases of the respective body members are mutually adapted to permit their interconnection in the field by simple means, such as threaded connectors. The body members are also keyed, e.g., by the interconnector means, to assure a fail safe assembly with the primary and secondary utility lines in proper registration. In the preferred embodiments, one or more external annular barbs are provided on each of the utility line fittings to provide secure linkage of the utility lines to the connector body. This expedient is particularly effective for resisting the separation of the secondary utility lines from the first body member which is otherwise induced by shipping and handling stresses.

BRIEF DESCRIPTION OF THE DRAWINGS

In the drawings, which illustrate what is presently regarded as the best mode of carrying out the invention.

DESCRIPTION OF THE ILLUSTRATED EMBODIMENT

Figure 1:
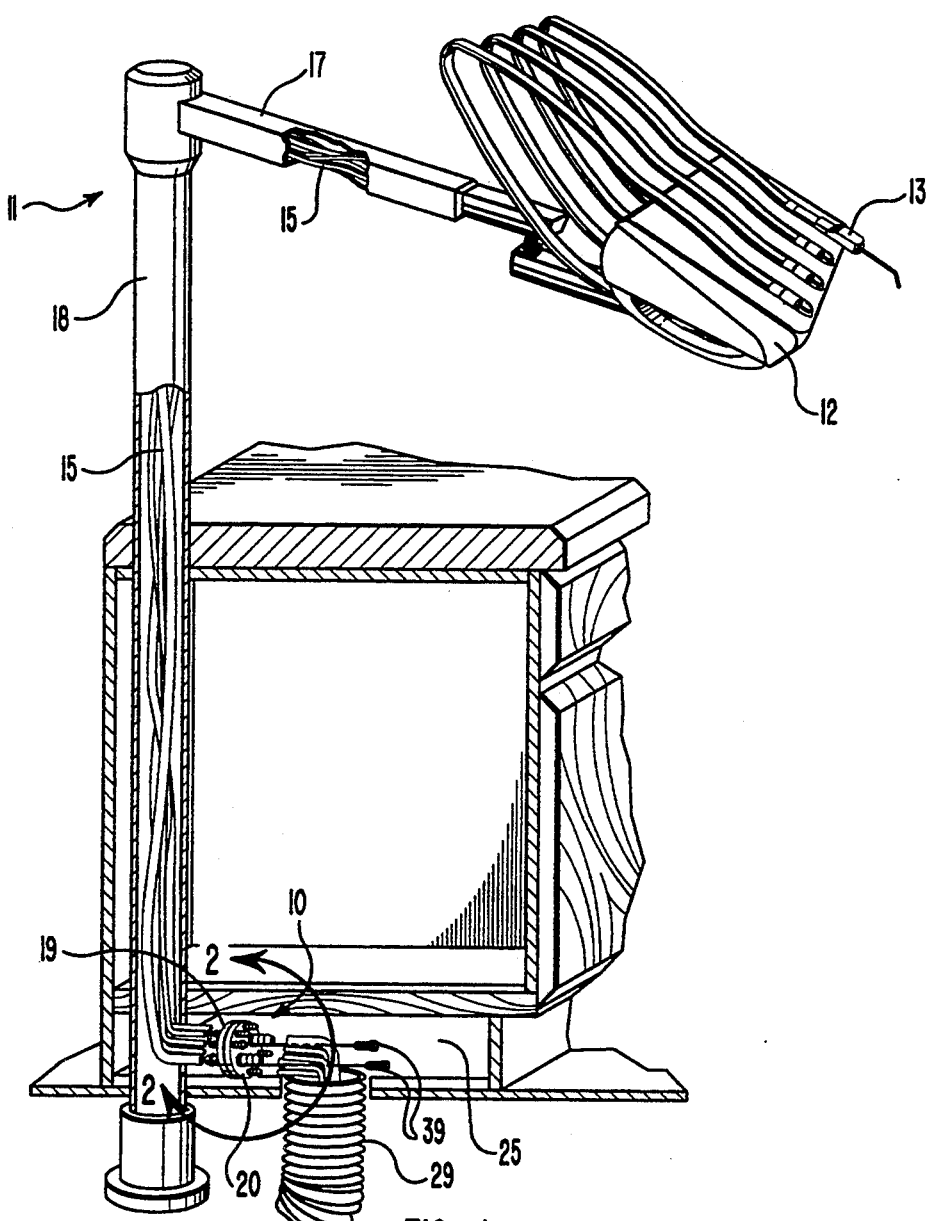
FIG. 1 is an exploded view of a dental delivery system incorporating a connector of the invention.

FIG. 1 illustrates a typical multi-line quick disconnect dental utility connector 10 of the present invention. The connector 10 is shown applied to a post mounted dental delivery system, indicated generally 11. A control head unit 12 is preassembled so that dental delivery hand units 13 are plumbed to utility line conduits 15. The conduits 15 are routed through an attached articulating support arm 17 and down a mounting post 18, eventually terminating at a first body member 19 of the multi-line connector 10. The connector 10 includes a second body member 20.

The utility line conduits 15 and the first body member 19 are sized and configured to fit and extend through the tubular support arm 17 and the mounting post 18. The post 18 is adapted to be fixed in an upright position at a permanent location in a dental office. Dental utilities, including water, air, drain and vacuum are preplumbed into a permanent utility center 25 as an umbilical 29. The utilities are connected to the hand units 13 by securing the hand unit utility line conduits 15 through connector 10 to the utility center umbilical 29.

Figure 2:
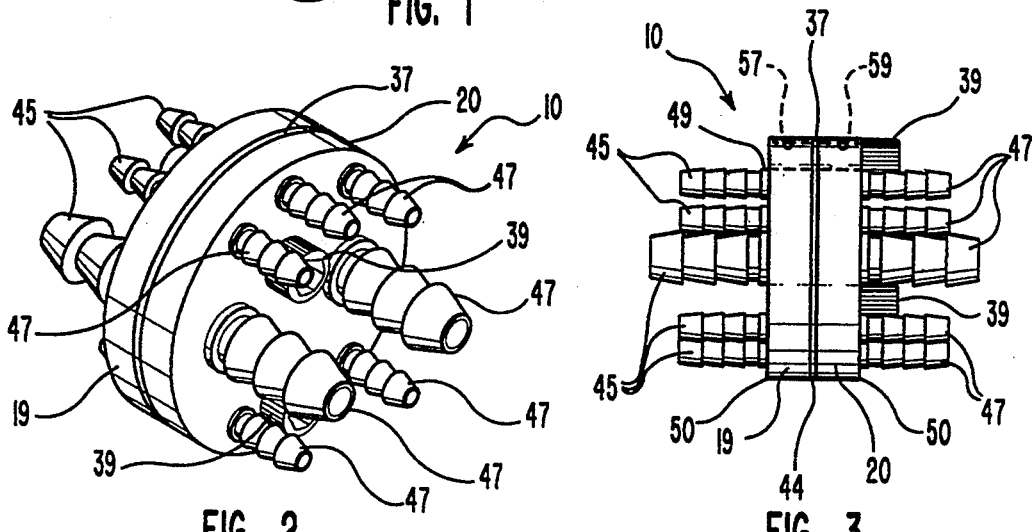
FIG. 2 is an enlarged, assembled perspective view of the quick disconnect multi-line connector of the system of FIG. 1.
Figure 3:
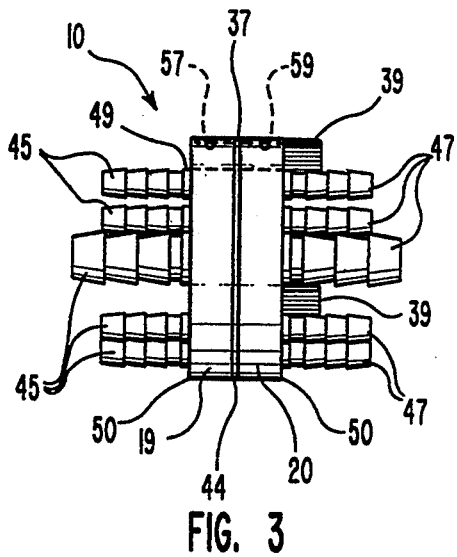
FIG. 3 is a view in side elevation of the quick disconnect multi-line connector of FIGS. 1 and 2 in its assembled configuration.

As best seen in FIGS. 2 and 3, the illustrated preferred embodiment of a multi-line dental utility connector 10 includes the first and second body members 19 and 20, a gasket 37, and screws 39 to fasten the body members together.

Figure 4:
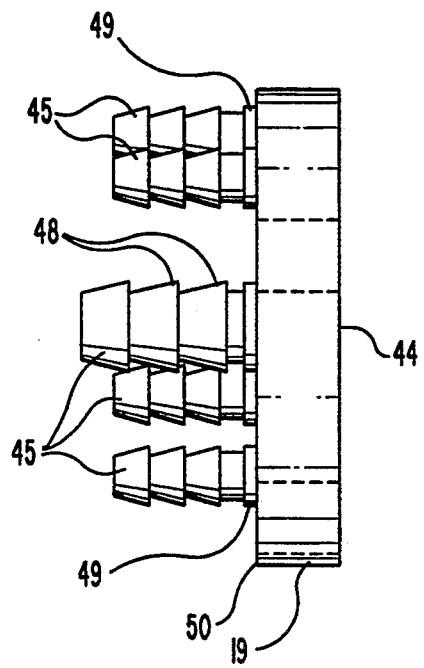
FIG. 4 is a side elevation view of a first body member of the quick disconnect multi-line connector of this invention.
Figure 5:
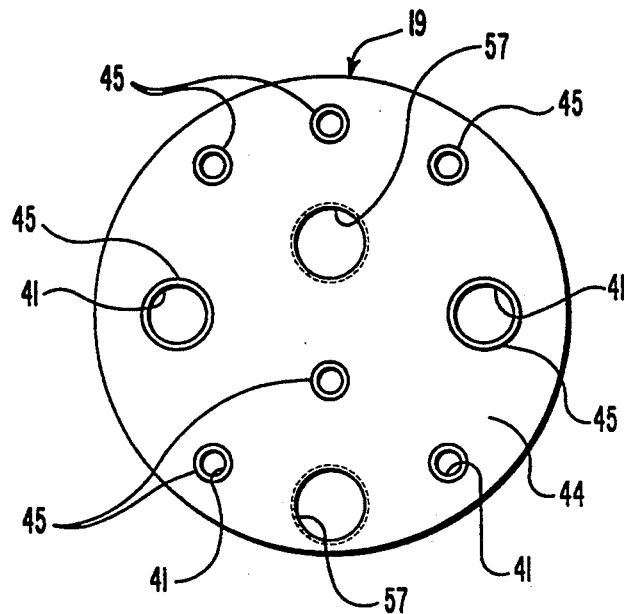
FIG. 5 is a front elevation view of the body member of FIG. 4.
Figure 6:
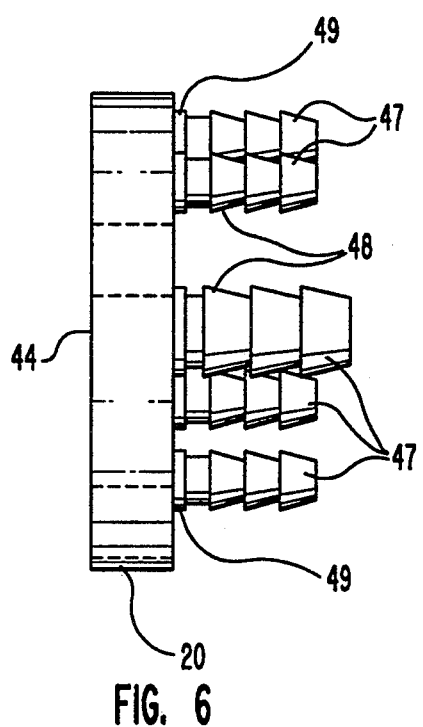
FIG. 6 is a side elevation view of a second body member of the present invention.
Figure 7:
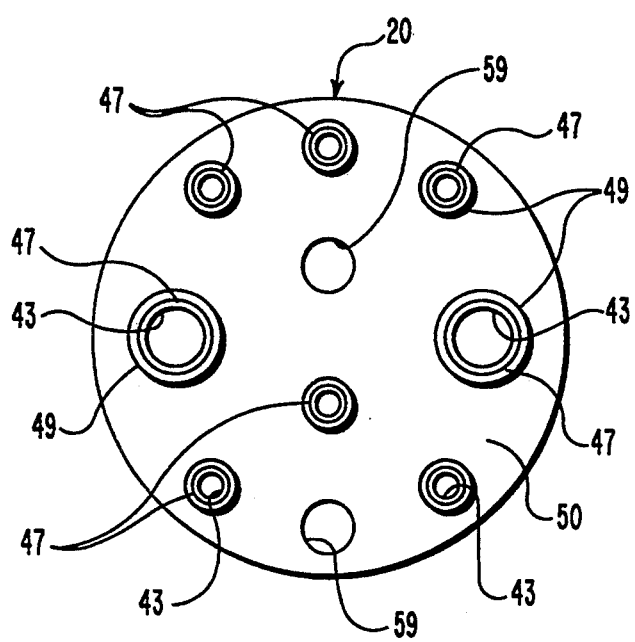
FIG. 7 is a front elevation view of the body member of FIG. 6.

Body member 19 (FIG. 4) includes spaced apart internal fluid passages 41 (FIG. 5). Body member 20 (FIG. 6) includes corresponding internal fluid passages 43 (FIG. 7). The passages 41, 43 are arranged in corresponding patterns. Thus, each passage 41 registers with the corresponding passage 43 when members 19, 20 are assembled as illustrated by FIGS. 2 and 3 with the mating surfaces 44 juxtaposed. Passages 41 are each in fluid communication with an attached fitting 45. Similarly, each passageway 43 is in fluid communication with an attached fitting 47. As illustrated, each of the fittings 45 and 47 is exteriorly configured with annular friction boss structures 48. The fittings 45, 47 are shown attached with solder rings 49 to the exterior surfaces 50 of the respective body members 19, 20 opposite the mating surfaces 44.

Figure 8:
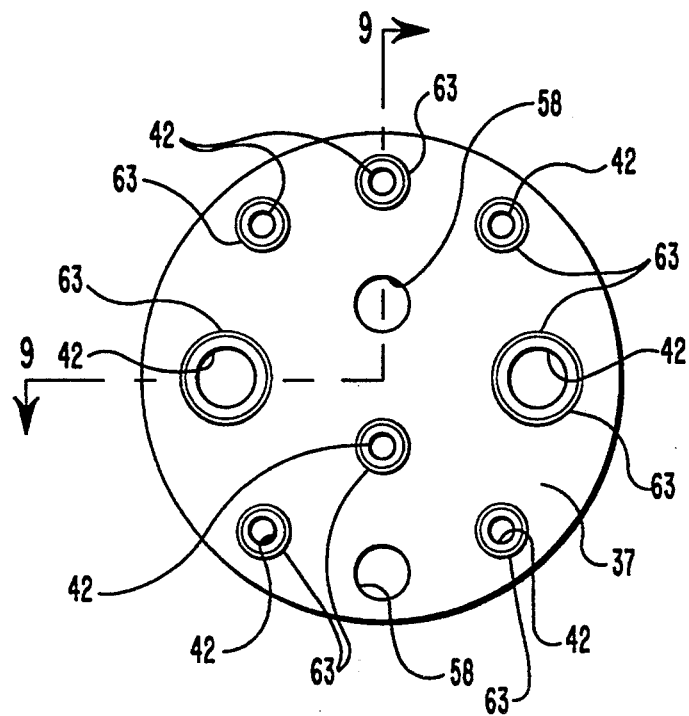
FIG. 8 is a front elevation view of a preferred gasket.
Figure 9:
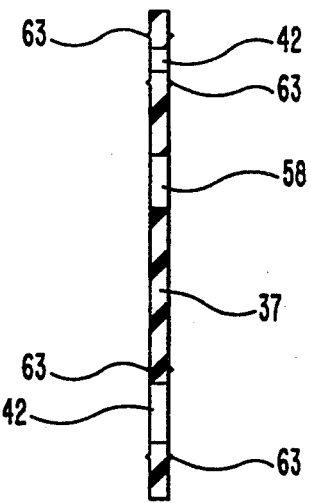
FIG. 9 is a view in section taken along the line 9—9 of FIG. 8.

Mating surface 44 (FIG. 4) of the first body member 19 is placed face to face with the mating surface 44 (FIG. 6) of the second body member 20. Gasket 37 (FIG. 2) is positioned between mating surfaces 44 of the body members 19, 20. Fluid passages 41, 43 through body members 19 and 20 and their attached fittings 45 and 47 are aligned to allow flow through the gasket fluid passages 42 (FIG. 8). Screws 39 (FIGS. 2 and 3) are inserted through holes 59 (FIG. 7) in the second body member 20 and 58 (FIG. 8) in the gasket 37, and are threaded into internally threaded holes 57 (FIG. 5) in the first body member 19. Fail safe registration of fluid passages 41, 42, 43 is assured by the asymmetric placement of the holes 57, 58, 59 for screws 39. The gasket 37 carries crush ribs 63 (FIG. 9) which provide a fluid tight seal around passages 41, 42, 43 at the interface of surfaces 44 with the gasket 37 (FIG. 3).

References to the preferred and illustrated embodiments are not intended to limit the scope of the appended claims which themselves recite those features regarded as important to the invention.

What is claimed is:

1. A connector in combination with a multi-line dental utility delivery system in which a source for utilities is separated from a handpiece control head by secondary supply lines fed through a hollow post, said connector comprising:

a first body member having a first planar mating surface at one side of said first body member, a plurality of spaced apart fittings projecting from a first exterior surface at the opposite side of said body member, a passage through each fitting continuing through said body member to said first planar surface;

a second body member having a second planar surface at one side of said second body member, a plurality of spaced apart fittings projecting from a second exterior surface at the opposite side of said second body member, a passage through each fitting continuing through said second body member to said second planar surface; and connection means for releasably holding said first and second planar surfaces in juxtaposed relationship with said fittings of said first body member projecting in the opposite direction of said fittings of said second body member, and with said passages through each fitting of said first body member aligned with a passage through a fitting of said second body member;

said first body member being configured and sized to permit its travel from end to end through the hollow interior of said post.

2. A connector as in claim 1, including gasket means between said first and second planar surfaces of said first and second body members, whereby to provide a fluid tight seal around each of said passageways at the interface between said first and second planar surfaces.

3. A connector as in claim 2, in which said connection means is constructed and arranged to assure the fail safe alignment of said passageways in said first and second body members when said first and second planar surfaces are held in juxtaposed position by said connection means.

4. A connector as in claim 1, wherein said first body member and said second body member each have spaced apart fastener holes therethrough, said fastener holes in said first body member being aligned with said fastener holes in said second body member when said passages through said fittings of each body member are aligned with said body member planar surfaces in face-to-face relationship; and wherein said fastener holes through one of said body members are threaded and said means for holding said planar surfaces in face-to-face relationship includes screws inserted through said fastener holes of said other body member and threaded into said threaded fastener holes.

5. A connector as in claim 1, further including at least one friction boss encircling each of said fittings at the ends thereof remote from the connection of said fittings and said body member.

6. For use in a dental operatory, the combination of
a tubular mounting post having one end adapted to be fixed to a predetermined location;
a tubular support arm or arms adapted to be attached to said tubular mounting post;
a plurality of conduits, each adapted to be connected for fluid flow therethrough;
a connector having a first body member with a plurality of passages extending therethrough, said plurality of conduits each being connected to said first body member at a passage therethrough, said first body member being sized to fit through each of said tubular post and arm, and a second body member having a plurality of passages therethrough;
means to releasably secure said first and second body member together with said passages through said first body member aligned with said passages of said second body member; and
means on said second body member for connecting fluid conduits thereto in alignment with said passages therethrough.

7. The combination of claim 6, wherein
said first body member has a first mating surface at one side of said first body member, a plurality of spaced apart fittings projecting from a first exterior face at an opposite side of said body member, a passage through each fitting aligned with one of said passages through said body member;
a second body member having a second mating surface at one side of said second body member, a plurality of spaced apart fittings projecting from a second exterior face at the opposite side of said second body member, a passage through each fitting aligned with one of said passages through said second body member; and
said means to releasably secure said first and second body members together holds said first and second body mating surfaces in face-to-face relationship with said fittings of said first body member projecting in a direction opposite to the projection of said fittings of said second body member, and with each of said passages through a fitting of said first body member aligned with a passage through a fitting of said second body member.

8. The combination of claim 7, wherein
said first body member and said second body member each have spaced apart fastener holes therethrough, and with said fastener holes in said first body member aligned with said fastener holes in said second body member when said passages through said body members are aligned and with said body member mating surfaces in face-to-face relationship, said fastener holes through one of said body members being threaded; and
wherein said means for holding said mating surfaces in face-to-face relationship comprises screws inserted into fastener holes of said other of said body members and into said threaded fastener holes.

9. The combination of claim 8, further including gasket means between said mating faces of said first and second body members, said gasket means having holes therethrough aligned with said passages and said fastener holes through said body members.

10. The combination of claim 8, further including at least one friction boss encircling each of said fittings at the ends thereof remote from the connection of said fittings and said body member.

* * * * *